United States Patent
Han et al.

(10) Patent No.: US 10,870,798 B2
(45) Date of Patent: Dec. 22, 2020

(54) HOMOGENEOUS PERSISTENT LUMINESCENCE NANOCRYSTALS AND METHODS OF PREPARATION AND APPLICATION THEREOF

(71) Applicant: University of Massachusetts, Boston, MA (US)

(72) Inventors: Gang Han, Shrewsbury, MA (US); Zhanjun Li, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 16/402,391

(22) Filed: May 3, 2019

(65) Prior Publication Data
US 2019/0292452 A1     Sep. 26, 2019

Related U.S. Application Data

(62) Division of application No. 15/553,863, filed as application No. PCT/US2016/020106 on Feb. 29, 2016, now Pat. No. 10,323,183.
(Continued)

(51) Int. Cl.
*A61K 8/27* (2006.01)
*C01G 15/00* (2006.01)
(Continued)

(52) U.S. Cl.
CPC .............. *C09K 11/682* (2013.01); *A61K 8/25* (2013.01); *A61K 8/27* (2013.01); *A61K 9/5115* (2013.01);
(Continued)

(58) Field of Classification Search
CPC ........ A61K 2800/412; A61K 2800/413; A61K 2800/434; A61K 8/25; A61K 8/27;
(Continued)

(56) References Cited

U.S. PATENT DOCUMENTS 9,877,653 B2 *   1/2018   Maldiney ........... A61K 49/0093

FOREIGN PATENT DOCUMENTS

WO       WO-2013113721 A1 *   8/2013   ............. A61B 90/39

OTHER PUBLICATIONS

Maldiney et al. (Nature Materials Apr. 2014;13:418-426). (Year: 2014).*

* cited by examiner

*Primary Examiner* — Ernst V Arnold
(74) *Attorney, Agent, or Firm* — Milstein Zhang & Wu LLC

(57) ABSTRACT

This invention provides a groundbreaking approach to PLNPs and their preparation. In particular, the synthetic methodology disclosed herein fundamentally differs from the traditional solid-state annealing reactions that require extreme and harsh reaction conditions. In one unique aspect of the invention, a simple, one-step mesoporous template method utilizing mesoporous silica nanoparticles (MSNs) is disclosed that affords in vivo rechargeable NIR-emitting mesoporous PLNPs with uniform size and morphology. In another unique aspect of the invention, the novel synthetic approach is based on aqueous-phase chemical reactions conducted in mild conditions, resulting in uniform and homogeneous PLNPs with desired size control (e.g., sub-10 nm).

7 Claims, 20 Drawing Sheets

Related U.S. Application Data

(60) Provisional application No. 62/127,376, filed on Mar. 3, 2015.

(51) Int. Cl.
    *C01B 21/20* (2006.01)
    *C09K 11/68* (2006.01)
    *A61K 8/25* (2006.01)
    *A61Q 3/02* (2006.01)
    *A61Q 5/06* (2006.01)
    *C09K 11/59* (2006.01)
    *A61K 9/51* (2006.01)
    *C09D 5/03* (2006.01)
    *C09D 5/22* (2006.01)
    *G01N 33/58* (2006.01)

(52) U.S. Cl.
    CPC .............. *A61Q 3/02* (2013.01); *A61Q 5/065* (2013.01); *C01G 15/00* (2013.01); *C09D 5/031* (2013.01); *C09D 5/22* (2013.01); *C09K 11/592* (2013.01); *G01N 33/587* (2013.01); *A61K 2800/412* (2013.01); *A61K 2800/413* (2013.01); *A61K 2800/434* (2013.01); *C01P 2002/72* (2013.01); *C01P 2004/04* (2013.01); *C01P 2004/54* (2013.01); *C01P 2004/62* (2013.01); *C01P 2004/64* (2013.01); *C01P 2006/12* (2013.01); *C01P 2006/60* (2013.01); *C01P 2006/82* (2013.01)

(58) Field of Classification Search
    CPC ........ A61K 9/5115; A61Q 3/02; A61Q 5/065; C01G 15/00; C01P 2002/72; C01P 2004/04; C01P 2004/54; C01P 2004/62; C01P 2004/64; C01P 2006/12; C01P 2006/60; C01P 2006/82; C09D 5/031; C09D 5/22; C09K 11/592; C09K 11/682; G01N 33/587

See application file for complete search history.

HOMOGENEOUS PERSISTENT LUMINESCENCE NANOCRYSTALS AND METHODS OF PREPARATION AND APPLICATION THEREOF

PRIORITY CLAIMS AND RELATED APPLICATIONS

This application is a divisional of and claims the benefit of priority to U.S. Ser. No. 15/553,863, filed Aug. 25, 2017, which is the U.S. national phase of and claims priority to PCT/US16/20106, filed Feb. 29, 2016, which claims the benefit of priority to U.S. Provisional Application Ser. No. 62/127,376, filed Mar. 3, 2015, the entire content of each of which is incorporated herein by reference in its entirety.

TECHNICAL FIELDS OF THE INVENTION

The invention generally relates to materials and methods for persistent luminescence. More particularly, the invention relates to uniform and homogeneous persistent luminescence nanoparticles, and methods of preparation and application thereof.

BACKGROUND OF THE INVENTION

Persistent luminescence (PL), also called afterglow or long-lasting phosphorescence, is the phenomenon encountered in materials that glow well after the end of an excitation with UV or visible light. PL materials have been used in a wide variety of applications, such as luminous dials and displays, fiber-optic thermometers, and forensic and military identification materials. While the mechanism underlying PL is not fully understood, it is generally agreed that the phenomenon involves energy traps in a material that are filled during excitation. After excitation, the stored energy is gradually released to emitter centers.

In near infrared (NIR) persistent luminescence, PL phosphors can store excitation energy in energy traps while continuing to emit photons for weeks after excitation ceases. (Pan, et al. 2012 *Nat Mater* 11, 58; Abdukayum, et al. 2013 *J Am Chem Soc* 135, 14125; Liu, et al. 2013 *Sci Rep-Uk* 3, 1554.) Studies have been done to explore advanced biomedical applications for NIR persistent luminescence nanoparticles (PLNPs) that can emit PL in the optical bio-imaging window (~650-1000 nm) for hours, or even days, after cessation of excitation. (Pan, et al. 2012 *Nat Mater* 11, 58; Maldiney, et al. 2014 *Nat Mater* 13, 418.) The temporal separation of excitation and afterglow properties of these persistent phosphors makes them ideal as in vivo optical imaging contrast reagents. (Chermont, et al. 2007 *P Natl Acad Sci USA* 104, 9266; Maldiney, et al. 2011 *J Am Chem Soc* 133, 11810; Maldiney, et al. 2011 *Acs Nano* 5, 854.) Excitation resource and relevant complicated optics that are necessary for traditional fluorescence imaging are no longer needed.

Until now, persistent luminescence has relied on short-wavelength excitation (e.g., ultraviolet light), which has rather limited tissue-penetration depth. (Clabau, et al. 2005 *Chem Mater* 17, 3904; Lin, et al. 2001 *J Mater Sci Lett* 20, 1505; Rodrigues, et al. 2014 *J Mater Chem C* 2, 1612; Rodrigues, et al. 2012 *J Phys Chem C* 116, 11232.) To address this problem, a NIR-light-stimulated PL mechanism was proposed in $LiGa_5O_8:Cr^{3+}$, to release energy trapped in deeper energy levels of the phosphor. In this case, however, the energy must be pre-charged by UV-light and the photo-stimulated emission continues to weaken after each cycle of photo-stimulation and finally becomes extinguished. (Liu, et al. 2013 *Sci Rep-Uk* 3, 1554; Zhuang, et al. 2013 *J Mater Chem C* 1, 7849.) Very recently, the PL phosphor, $ZnGa_2O_4:Cr^{3+}$ (ZGC), was found to be activatable using tissue-penetrable red light, which means that energy can be recharged and NIR PL imaging is no longer limited by the luminescence-decay life-time of the phosphor. (Maldiney, et al. 2014 *Nat Mater* 13, 418.) Thus ZGC is arguably the optimal rechargeable NIR persistent emitting phosphor reported to date.

Despite such inspiring progress, production of uniformly structured NIR PL ZGC phosphors remains challenging. Advances in the development of PLNPs for both basic research and commercialization have been hampered by their complicated synthesis methods. To make such NIR-persistent phosphors bulk crystal requires temperatures greater than 750° C. in traditional solid-state annealing reactions. (Pan, et al. 2012 *Nat Mater* 11, 58; Clabau, et al. 2005 *Chem Mater* 17, 3904; Setlur, et al. 2008 *J Appl Phys* 103, 053513.) Moreover, to convert such bulk crystal into nanoparticles that are sufficiently disperse for biological applications, certain tedious physical treatments such as grinding or laser ablation must be utilized. (Abdukayum, et al. 2013 *J Am Chem Soc* 135, 14125; Liu, et al. 2013 *Sci Rep-Uk* 3, 1554; Maldiney, et al. 2014 *Adv Funct Mater* DOI 10.1002/adfm.201401612; Maldiney, et al. 2014 *Nanoscale* 6 (22), 13970-13976; Maldiney, et al. 2012 *Opt Mater Express* 2, 261.) The afforded products are generally highly heterogeneous and suffer from severe agglomeration. In addition, bio-imaging applications generally require that the nanocrystals be biocompatible, which means that the PLNPs need to be comparable in size to the biomolecules they label, so as not to interfere with cellular systems.

Thus, novel and improved synthetic methodologies, in particular aqueous-phase chemical synthesis for sub-10 nm NIR PLNPs that are uniform and can be homogeneously dispersed in a carrying medium (e.g., aqueous solution), are strongly desired.

SUMMARY OF THE INVENTION

The invention provides novel PLNPs that are uniform and homogeneous, aqueous-phase chemical synthesis of such PLNPs, and their applications in various fields including biomedical, cosmetics, plastics, inks, security, etc.

In one aspect, the invention generally relates to a method for preparing mesoporous persistent luminescence nanoparticles. The method includes providing mesoporous silica nanoparticles having mesopores of defined size and morphology; and reacting precursors to form persistent luminescent nanoparticles templated by the mesopores of the mesoporous silica nanoparticles under conditions sufficient to form mesoporous persistent luminescence nanoparticles.

In another aspect, the invention generally relates to mesoporous persistent luminescence nanoparticles prepared by a method disclosed herein.

In yet another aspect, the invention generally relates to a method for preparing persistent luminescence nanoparticles. The method includes conducting a hydrothermal chemical reaction in an aqueous phase under conditions sufficient to form uniform and homogeneous persistent luminescence nanoparticles.

In yet another aspect, the invention generally relates to persistent luminescence nanoparticles prepared by a method according to a method disclosed herein.

In yet another aspect, the invention generally relates to rechargeable persistent luminescence nanocomposites comprising doped zinc gallates $ZnGa_2O_4$:Cr that are substantially uniform and homogeneous with a median particle size of less than about 1,000 nm and having specific surface area from about 50 $m^2/g$ to about 600 $m^2/g$ wherein the mesoporous persistent luminescence nanocomposites is capable of NIR-emitting in the range from about 650 nm to about 900 nm after multiple emission and recharge cycles (e.g., greater than 5, greater than 10).

DETAILED DESCRIPTION OF THE INVENTION

Figure 1:
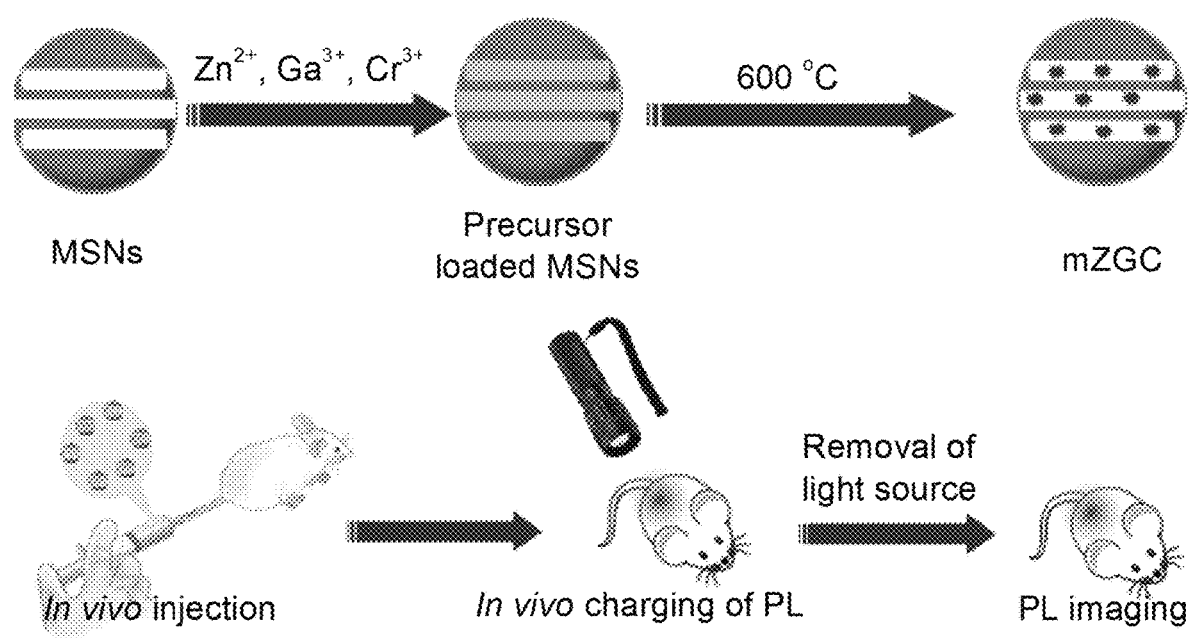
FIG. 1. Illustration of the synthesis of PL-functionalized MSNs and their in vivo imaging application.

This invention provides a groundbreaking approach to PLNPs and their preparation. In particular, the synthetic methodology disclosed herein fundamentally differs from the traditional solid-state annealing reactions that require extreme and harsh reaction conditions.

In one unique aspect of the invention, a simple, one-step mesoporous template method utilizing mesoporous silica nanoparticles (MSNs) is disclosed that affords in vivo rechargeable NIR-emitting mesoporous PLNPs with uniform size and morphology.

For example, uniform sized NIR-emitting mesoporous $SiO_2$/$ZnGa_2O_4$:$Cr^{3+}$ persistent luminescence nanocomposites were made by a simple, one-step mesoporous template method. The near-infrared persistent luminescence of the nanocomposites can be recharged for multiple times both in vitro under deep tissue simulation (e.g., 8 mm pork slab) and in a live mouse model. This unconventional approach paves the way for the synthesis and wider application of deep tissue rechargeable ZGC persistent luminescence materials in photonics and biophotonics.

In another unique aspect of the invention, the novel synthetic approach is based on aqueous-phase chemical reactions conducted in mild conditions, resulting in uniform and homogeneous PLNPs with desired size control (e.g., sub-10 nm). The PLNPs can be homogeneously dispersed in a carrying medium (e.g., aqueous solution).

For example, the aqueous phase synthesis afforded uniformed NIR PL ZGC nanoparticles. The synthesis temperature was significantly decreased from up 1000° C. needed for existing methods to around 250° C., which greatly simplifies the reaction equipment. The as-synthesized ZGC nanocrystals can be made as small as a size of 8±4 nm with narrow size distribution, which is important for its potential biomedical applications. The ZGC nanocrystals can be easily distributed into water after a simple acid washing posttreatment, which facilitates its surface modification of diverse functional group including biomolecules (e.g., antibody). It has been demonstrated that the PLNPs so prepared provide significantly better PL intensity than those synthesized by the traditional annealing method and can be activated in deep tissue covered by 1 cm pork layer, which enables it for various in vivo applications.

In one aspect, the invention generally relates to a method for preparing mesoporous persistent luminescence nanoparticles. The method includes providing mesoporous silica nanoparticles having mesopores of defined size and morphology; and reacting precursors to form persistent luminescent nanoparticles templated by the mesopores of the mesoporous silica nanoparticles under conditions sufficient to form mesoporous persistent luminescence nanoparticles.

In certain embodiments of the invention, the specific surface area of the mesoporous silica nanoparticles is from about 100 m$^2$/g to about 2,000 m$^2$/g (e.g., from about 100 m$^2$/g to about 1,000 m$^2$/g, from about 100 m$^2$/g to about 800 m$^2$/g, from about 100 m$^2$/g to about 600 m$^2$/g, from about 100 m$^2$/g to about 400 m$^2$/g, from about 200 m$^2$/g to about 2,000 m$^2$/g, from about 500 m$^2$/g to about 2,000 m$^2$/g, from about 800 m$^2$/g to about 2,000 m$^2$/g, from about 1,000 m$^2$/g to about 2,000 m$^2$/g).

In certain embodiments of the invention, the mesoporous persistent luminescence nanoparticles are NIR-emitting in the range of about 650 nm to about 900 nm.

In certain embodiments of the invention, the mesoporous persistent luminescence nanoparticles are rechargeable.

In certain embodiments of the invention, the mesoporous persistent luminescence nanoparticles are doped zinc gallates $ZnGa_2O_4$:Cr.

In certain embodiments of the invention, reacting precursors to form persistent luminescent nanoparticles is conducted at a temperature in a range from about 400° C. to about 700° C. (e.g., from about 400° C. to about 650° C., from about 400° C. to about 600° C., from about 400° C. to about 550° C., from about 400° C. to about 500° C., from about 450° C. to about 700° C., from about 500° C. to about 700° C., from about 550° C. to about 700° C., from about 600° C. to about 700° C.).

In certain embodiments of the invention, wherein persistent luminescence is detectable at least 5 hours (e.g., at least 10 hours) after excitation.

In certain embodiments of the invention, the formed persistent luminescent nanoparticles are substantially uniform and homogeneous with median particle sizes less than about 1,000 nm (e.g., less than about 500 nm, less than about 200 nm, less than about 100 nm, less than about 50 nm, less than about 20 nm, less than about 10 nm).

In another aspect, the invention generally relates to mesoporous persistent luminescence nanoparticles prepared by a method disclosed herein.

In yet another aspect, the invention generally relates to a method for preparing persistent luminescence nanoparticles. The method includes conducting a hydrothermal chemical reaction in an aqueous phase under conditions sufficient to form uniform and homogeneous persistent luminescence nanoparticles.

In certain embodiments of the invention, the hydrothermal chemical reaction is conducted in aqueous phase at a temperature from about 150° C. to about 300° C. (e.g., from about 150° C. to about 280° C., from about 150° C. to about 250° C., from about 150° C. to about 230° C., from about 150° C. to about 200° C., from about 180° C. to about 300° C., from about 200° C. to about 300° C., from about 250° C. to about 300° C.).

In certain embodiments of the invention, the formed persistent luminescent nanoparticles are substantially uniform in particle size of less than about 10 nm (e.g., less than about 8 nm, less than about 6 nm, less than about 5 nm).

In certain embodiments of the invention, the persistent luminescence nanoparticles are NIR-emitting in the range from about 650 nm to about 900 nm (e.g., from about 650 nm to about 850 nm, from about 650 nm to about 800 nm, from about 650 nm to about 750 nm, from about 750 nm to about 900 nm, from about 800 nm to about 900 nm).

In certain embodiments of the invention, the mesoporous persistent luminescence nanoparticles are doped zinc gallates $ZnGa_2O_4$:Cr.

In certain embodiments of the invention, persistent luminescence is detectable at least 5 hours (e.g., at least 10 hours) after excitation.

In certain embodiments of the invention, the specific surface area of the mesoporous silica nanoparticles is from about 100 m$^2$/g to about 2,000 m$^2$/g (e.g., from about 100 m$^2$/g to about 1,000 m$^2$/g, from about 100 m$^2$/g to about 800 m$^2$/g, from about 100 m$^2$/g to about 600 m$^2$/g, from about 100 m$^2$/g to about 400 m$^2$/g, from about 200 m$^2$/g to about 2,000 m$^2$/g, from about 500 m$^2$/g to about 2,000 m$^2$/g, from about 800 m$^2$/g to about 2,000 m$^2$/g, from about 1,000 m$^2$/g to about 2,000 m$^2$/g).

In yet another aspect, the invention generally relates to persistent luminescence nanoparticles prepared by a method according to a method disclosed herein.

In yet another aspect, the invention generally relates to rechargeable persistent luminescence nanocomposites comprising doped zinc gallates $ZnGa_2O_4$:Cr that are substantially uniform and homogeneous with a median particle size of less than about 1,000 nm and having specific surface area from about 50 m$^2$/g to about 600 m$^2$/g wherein the mesoporous persistent luminescence nanocomposites is capable of NIR-emitting in the range from about 650 nm to about 900 nm after multiple emission and recharge cycles (e.g., greater than 5, greater than 10).

In certain embodiments of the invention, the rechargeable persistent luminescence nanocomposites are rechargeable in vivo by tissue-penetrable red excitation.

In certain embodiments of the invention, the specific surface area of the mesoporous silica nanoparticles is from about 50 m$^2$/g to about 600 m$^2$/g (e.g., from about 50 m$^2$/g to about 500 m$^2$/g, from about 50 m$^2$/g to about 300 m$^2$/g, from about 50 m$^2$/g to about 200 m$^2$/g, from about 50 m$^2$/g to about 100 m$^2$/g, from about 100 m$^2$/g to about 600 m$^2$/g, from about 200 m$^2$/g to about 600 m$^2$/g, from about 300 m$^2$/g to about 600 m$^2$/g, from about 400 m$^2$/g to about 600 m$^2$/g).

In certain embodiments of the invention, the median particle sizes are less than about 1,000 nm (e.g., less than about 500 nm, less than about 200 nm, less than about 100 nm, less than about 50 nm, less than about 20 nm, less than about 10 nm).

In certain embodiments of the invention, the persistent luminescence nanocomposites can emit multiple colors (2, 3, 4 or more colors).

In certain embodiments of the invention, the persistent luminescence nanocomposites are components of an imaging or diagnostic probe or a labeling agent for biomedical assays (e.g., western blot).

In certain embodiments of the invention, the persistent luminescence nanocomposites are components of a drug delivery vehicle or a therapeutic agent.

In certain embodiments of the invention, the persistent luminescence nanocomposites are components of a nail polish.

In certain embodiments of the invention, the persistent luminescence nanocomposites are components of a hair spray.

In certain embodiments of the invention, the persistent luminescence nanocomposites are components of ink for latent fingermark, and for art illustration and paints, tracer in dark conditions such as at night and submarine condition, for constructions, living goods and utility device.

In certain embodiments of the invention, the rechargeable persistent luminescence nanocomposites are homogenously dispersed in a solution or suspension of water or an organic solvent.

I. One-Step Templated Synthesis of NIR-Emitting Mesoporous PLNPs

Because of their readily controllable synthesis and resulting morphology, super-high specific surface area, huge pore volume, and good biocompatibility, MSNs are widely utilized in biology, drug delivery, and medicinal applications to encase various functional molecules/luminescence contrast reagents. (Yamashita, et al. 2013 *Advanced Drug Delivery Reviews* 65, 139; Liu, et al. 2013 *Angew Chem Int Edit* 52, 4375; Fan, et al. 2014 *Biomaterials* 35, 8992.)

As first disclosed herein, MSNs can be used to template the synthesis of ZGC NIR persistent phosphors in situ with defined size and morphology (mZGC). Since temperatures beyond 750° C. may lead to the collapse of the mesoporous silica nanostructures, the reaction temperature for the phosphor synthesis was explored systematically in this study. It was found that at 600° C., the as-synthesized mZGC preserves defined size, morphology and mesoporous nanostructure of the MSNs as well as possessing optimal luminescence properties. Further, the performance of mZGC in imaging was measured both in vitro and in vivo to assess potential applications in biophotonics. It was demonstrated that as-synthesized mZGC can be recharged in a simulated deep-tissue environment (~8 mm pork slab) in vitro using red light. Moreover, it was observed that mZGC can be repeatedly activated in vivo for persistent luminescence imaging in a live mouse model using white LED as a light source.

Formation of mZGC Using MSNs as Nanoreactors

Figure 8:
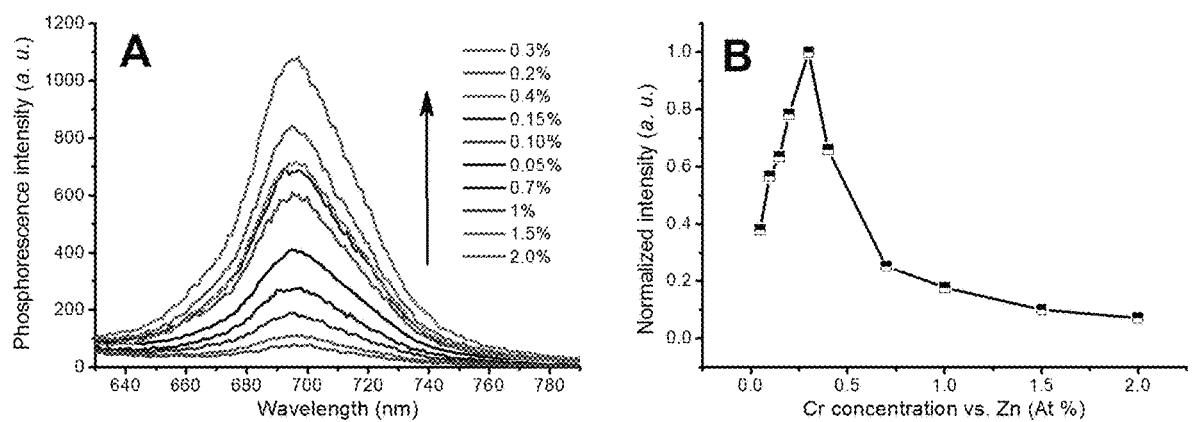
FIG. 8. Optimization of $Cr^{3+}$ doping concentration (vs. Zn) in mZGC.

The MSNs were impregnated with ZGC nitrate precursor solutions, which entered the nanochannels of MSNs with ease due to the capillarity of the mesopores. The optimal used composition was determined at Zn/Ga/Cr=1/1.997/0.003 by molar ratio (FIG. 8). ZGC was formed in the nanochannels of the MSNs after vacuum drying and annealing, as shown in FIG. 1. By measuring the mass of the used silica and the total mass of the as-formed nanocomposites, the content of ZGC in mZGC was calculated to be 10.4% by weight. (Table 1). Such a simple, one-step mesoporous template method allowed preparation of NIR-persistent-luminescent mesoporous nanocomposites that combine the unique optical properties of NIR persistent phosphors and the mesoporous attributes of mesoporous silica.

TABLE 1

Test of the ZGC content in as-synthesized mZGC product

| MSNs | mZGC | Increased mass | ZGC content in mZGC (by weight) |
|---|---|---|---|
| 400.0 mg | 445.7 mg | 45.7 mg | 10.4% ± 0.4% |
| 400.0 mg | 448.1 mg | 48.1 mg | |
| 400.0 mg | 445.4 mg | 45.4 mg | |

TABLE 2

Mass loss of mZGC after rinsed in PBS for 48 hours

| mZGC | Rinsed and dried mZGC | decreased mass | Mass loss by weight |
|---|---|---|---|
| 100.0 mg | 99.7 mg | −1.7 mg | 0.2% ± 1.5% |
| 100.0 mg | 101.4 mg | +1.4 mg | |
| 100.0 mg | 100.1 mg | +0.1 mg | |

X-ray diffraction (XRD) and luminescence measurements were used to confirm the nature of the as-synthesized nanocomposite. The XRD results (FIG. 2A) showed that the diffraction characteristics (peaks at 30.4°, 35.78°, 43.50°, 57.48°, 63.12°) of the ZGC crystal already appear when the annealing temperature reaches 500° C., which then become clear when the temperature increases to 600° C. This is in agreement with the presence of the spinel phase $ZnGa_2O_4$ (JCPDS index no. 01-086-0410). However, impurity peaks start to appear at 700° C., which indicate the formation of metal silicates (arrows in FIG. 2A). As a result, it was observed that the PL intensity (FIG. 2B; 650-750 nm) initially increases with temperature (from 400-600° C.) and reaches the optimal intensity at 600° C. before decreasing at 700° C.

Figure 2:
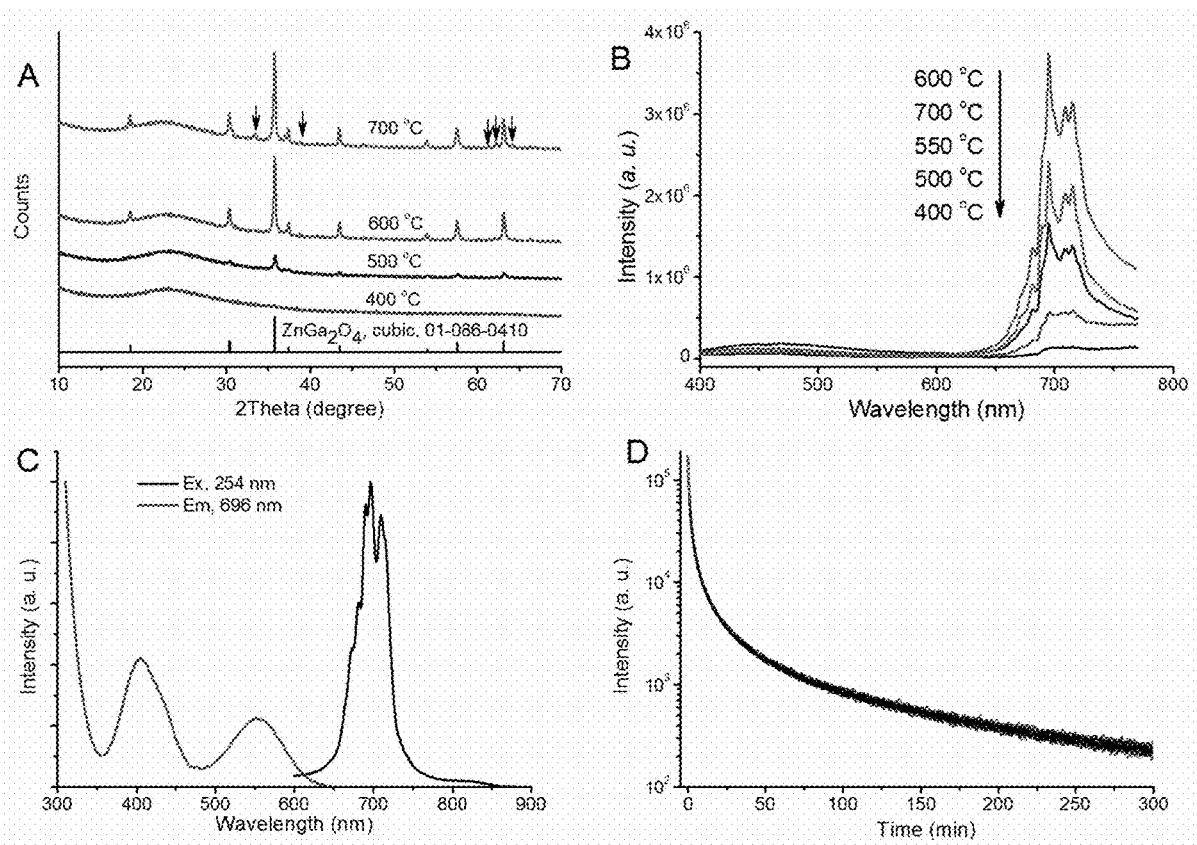
FIG. 2. Optimization of the experimental conditions. (A) XRD and (B) photoluminescence spectra (excitation wavelength, 254 nm) of the mZGC samples synthesized at various temperatures, (C) PL excitation and emission spectra (tested using the phosphorescence mode of the fluorimeter), (D) PL decay curve of mZGC synthesized at 600° C., excited by UV lamp (254 nm). Sample mass for above measurements is 100 mg.

The phosphorescence excitation spectrum of the sample synthesized at 600° C. consists of three ZGC characteristic excitation bands (FIG. 2C). These bands, which range from <350 nm, 350-470, and 470-650 nm, can be attributed to the band-to-band transitions of $ZnGa_2O_4$, $^4A_2\rightarrow^4T_1$, and the $^4A_2\rightarrow^4T_2$ transition of Cr', respectively. (Bessiere, et al. 2011 *Opt Express* 19, 10131.) Among these bands, the absorbance at 600-650 nm is responsible for the in vivo recharging using deeper-tissue-penetrating red light. (Maldiney, et al. 2014 *Nat Mater* 13, 418.) The PL spectrum (FIG. 2C) of the mZGC, which is around 696 nm (inside the NIR imaging window, which ranges from 650-900 nm), is also consistent with the results found in the traditional solid-state reaction. (Bessiere, et al. 2011 *Opt Express* 19, 10131; Zhuang, et al. 2013 *Appl Phys Express* 6. 052602; Zhuang, et al. 2014 *J Mater Chem C* 2, 5502.) The PL of ZGC can be detected even after more than 5 h followed by an excitation for 5 min with a UV light source (254 nm; FIG. 2D). Synthesis of zinc gallate based phosphors can usually only occur at temperatures at least 750° C. (Bessiere, et al. 2011 *Opt Express* 19, 10131; Zhuang, et al. 2013 *Appl Phys Express* 6. 052602; Allix, et al. 2013 *Chem Mater* 25, 1600.)

The decrease in synthesis temperatures from those generally used implies that the utilization of the pores of MSNs as nanoreactors facilitates the formation of ZGC phosphor. (A. R. West, Solid-State Chemistry and Its Applications (second edition), *John Wiley & Sons, Ltd*, 2014, 187.) Homogeneous distribution of these reactants in confined mesoporous nanostructures results in a higher reactivity than would otherwise be the case; such phenomena were observed previously. (Zhan-Jun, et al. 2012 *J Mater Chem* 22, 24713; Chen, et al. 2014 *Adv Mater* 26, 4947; Li, et al. 2014 *Opt Express* 22, 10509; Li, et al. 2014 *Green Chem* 16, 2680.)

Morphology and Porous Structure of mZGC

This substantial decrease in synthesis temperature is of vital importance to generate mZGC nanocomposites successfully since the nanochannels of MSNs start to collapse when annealed at temperatures higher than 600° C. (Li, et al. 2013 *Micropor Mesopor Mat* 176, 48.) The field-emission scanning electron microscopy (FESEM) images of the as-synthesized MSNs (FIG. 3A) and the corresponding mZGC (FIG. 3B) indicate that the MSNs survive calcination at 600° C. No apparent morphological change could be observed. Furthermore, in the transmission electron microscopy (TEM) and high-resolution-TEM (HRTEM) images (FIG. 3C, 3D), tiny dark spots (ZGC nanoparticles) appear homogeneously in the nanochannels of the MSNs.

Figure 3:
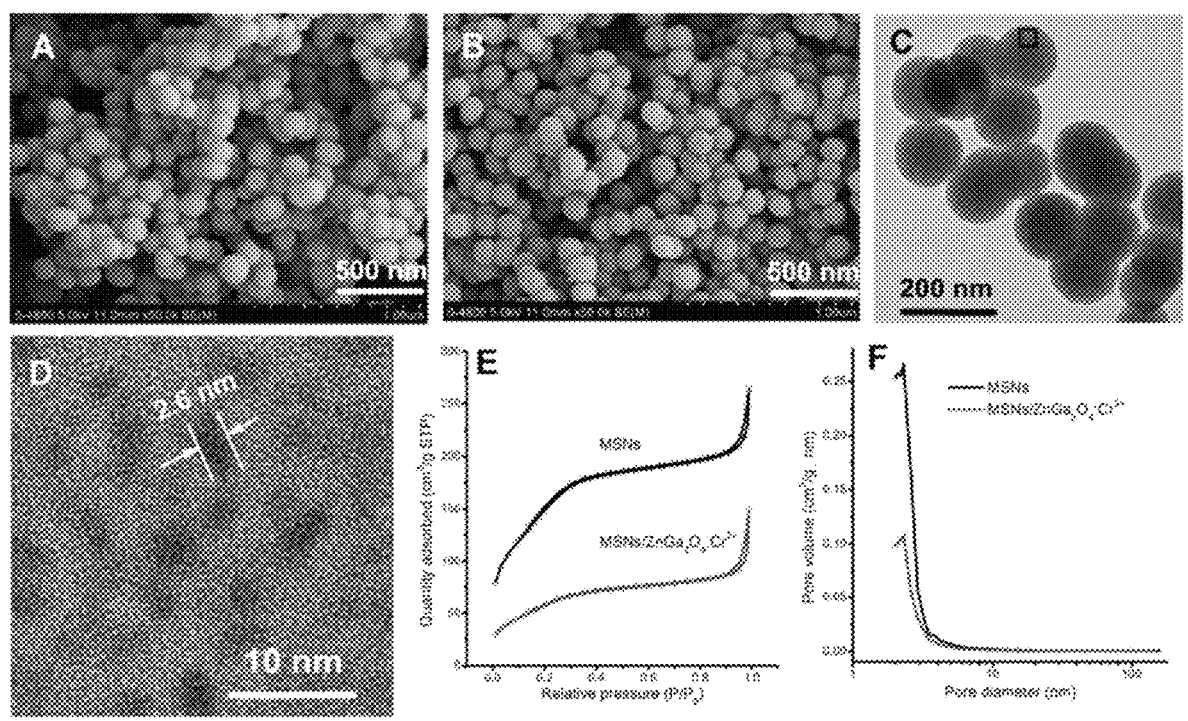
FIG. 3. Morphologies and porous structure of MSNs and mZGC. FESEM images of (A) MSNs and (B) mZGC. (C) TEM and (D) HRTEM images of mZGC, (E) $N_2$ adsorption/desorption isotherms, and (F) pore-size distributions of MSNs and mZGC.
Figure 9:
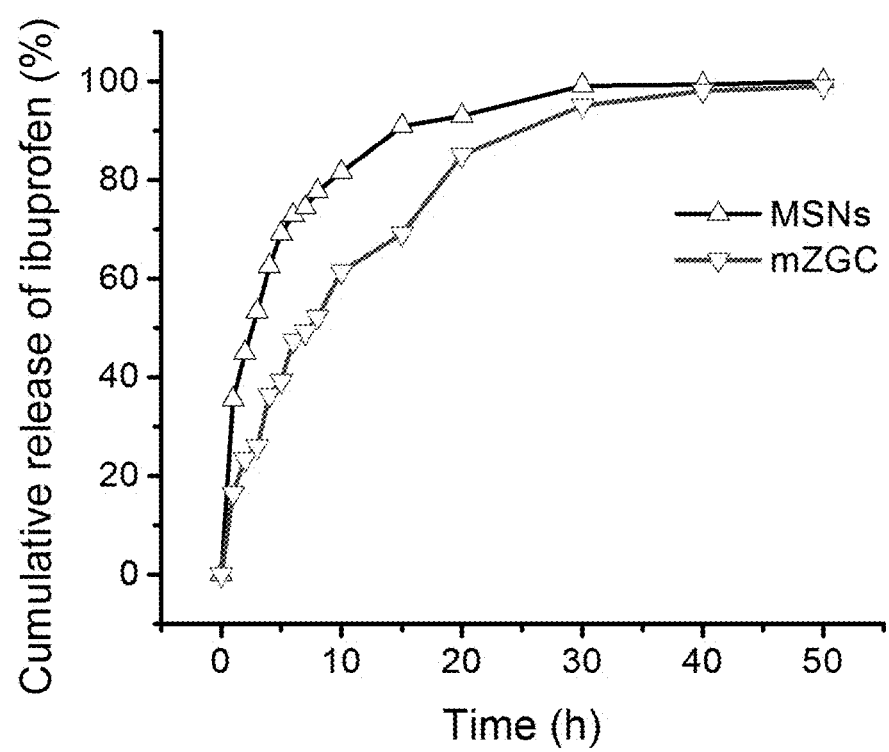
FIG. 9. Ibuprofen storage/release properties of mZGC. The ibuprofen storage and release experiment was performed according to a previous report. Briefly, 60 mg of the MSNs/$ZnGa_2O_4$:$Cr^{3+}$ were immersed into 1 mL of 20 mg/L ibuprofen cyclohexane solution for 24 h. Excess ibuprofen cyclohexane solution was removed by centrifugation and decantation. The cyclohexane in the mesoporous silica was evaporated in a 50° C. air dryer for 1 h. The in vitro release of ibuprofen was performed by immersing 60 mg of the drug loaded mZGC in 60 mL of simulated body fluid at 37° C. 100 μL of the mixed solution was taken to test the released amount of ibuprofen at fixed time intervals; this was centrifuged to determine the released ibuprofen in the supernatant by detecting the absorbance. The initial content of ibuprofen on MSNs and mZGC is 146.3 mg/g and 103.9 mg/g respectively, by elemental analysis.

$N_2$ adsorption/desorption was performed to study the influence of the synthesis process on the specific surface area and pore-size distribution of the MSNs. Apparent mesoporous characteristics of plateau regions can be observed both for the MSN templates and for the as-synthesized mZGC (FIG. 3E). The specific surface area of the MSNs according to the Brunauer-Emmett-Teller (BET) method decreased from 554.2 $m^2/g$ to 214.6 $m^2/g$, while the pore volume decreased from 0.3395 $cm^3/g$ to 0.1562 $cm^3/g$, which might arise from the formation of particles in the mesopores. The synthesis of mZGC from the MSNs did not decrease the overall average pore size of the carriers. In fact, a slight increase in average pore size from 2.450 nm to 2.912 nm was observed, as shown in FIG. 3F, which may be explained by the ZGC existing as isolated, tiny particles in the nanochannels of the MSNs, and this is also evidenced by the HRTEM image. The mesoporous properties of the as-synthesized mZGC were also verified by the sustained release of a widely used model cargo, ibuprofen (FIG. 9). Thus, the PL nano-carrier approach disclosed herein synergized both unique optical properties of ZGC and the cargo storage/release properties of MSNs.

Imaging Capability of mZGC Through Simulated Deep Tissue

Figure 4:
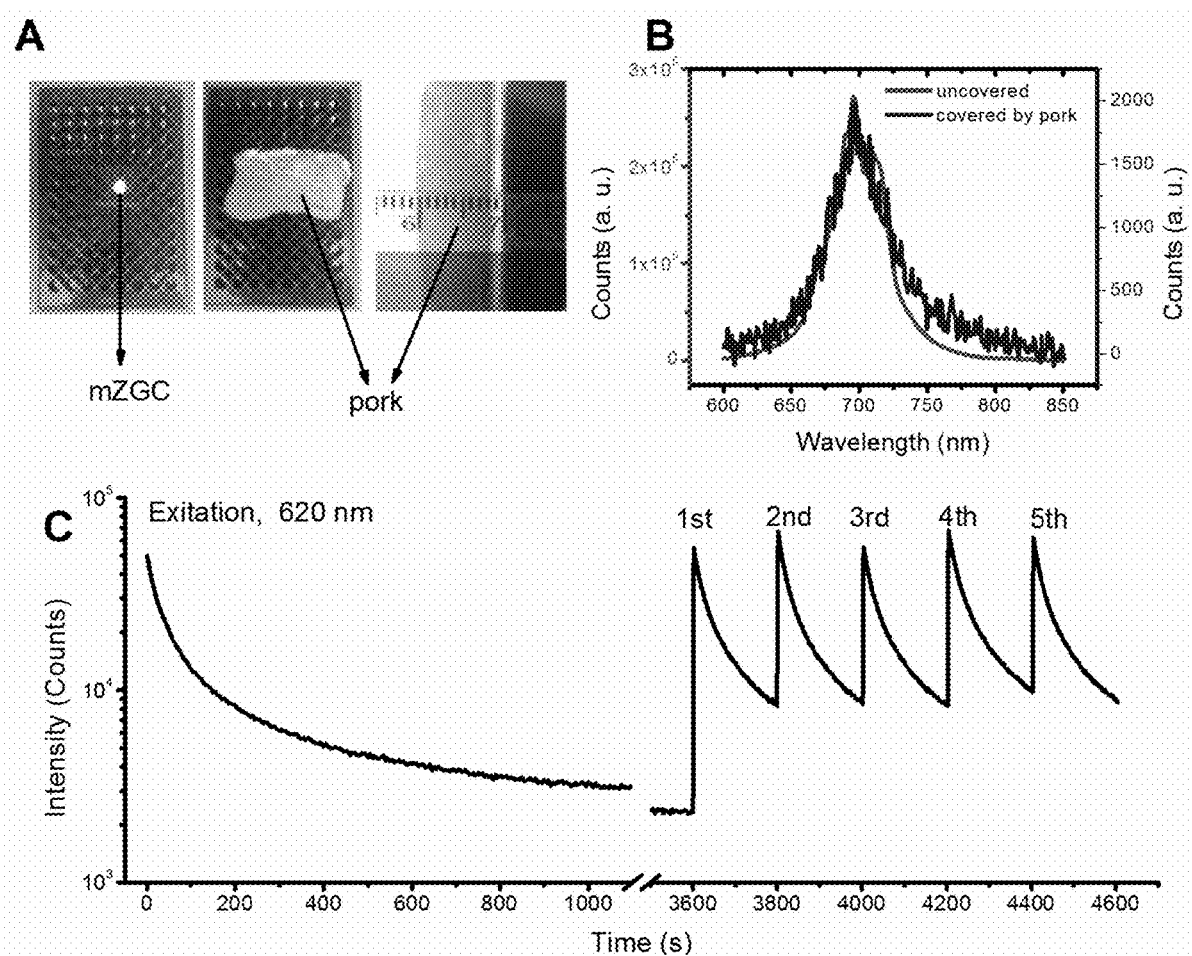
FIG. 4. In situ simulated deep-tissue charging properties of mZGC. (A) Optical image of in situ excitation, (B) PL spectra covered and uncovered by pork layer, (C) in vitro charged and recharged decay curves of mZGC. All spectra were recorded with the ZGC under an 8-mm pork layer.

Most of the current PL phosphors can only be excited effectively under blue or even UV light, which can hardly penetrate the deep tissue of animals. (Pan, et al. 2012 *Nat Mater* 11, 58; Chermont, et al. 2007 *P Natl Acad Sci USA* 104, 9266; Clabau, et al. 2005 *Chem Mater* 17, 3904.) The PL excitation band from 600-650 nm is in the transmission window of biological tissue (600-1100 nm) and thus gives us the opportunity to recharge the energy-exhausted mZGC in deep tissue in situ. (Maldiney, et al. 2014 *Nat Mater* 13, 418.) Since there is no standard method to accurately evaluate the deep-tissue-imaging ability of PL phosphors, a meat-covering method is proposed for comparison according to our previous report on up-conversion imaging (FIG. 3A). (Chen, et al. 2012 *Acs Nano* 6, 8280.) The as-synthesized mZGC sample disk could be excited at 620 nm when covered by 8 mm of pork. After switching off the light used for excitation, the PL spectrum can recorded using a fluorospectrometer (FluoroMax-3, HORIBA, USA) fitted with a photomultiplier tube (PMT) detector. A similar PL spectrum can be obtained to that of the uncovered sample, which means that the NIR PL of mZGC can efficiently penetrate pork tissue as thick as 8 mm, as shown in FIG. 4B. The in situ excited PL of mZGC could be reproduced consecutively in situ more than five times on any occasion, as shown in FIG. 4C.

Figure 5:
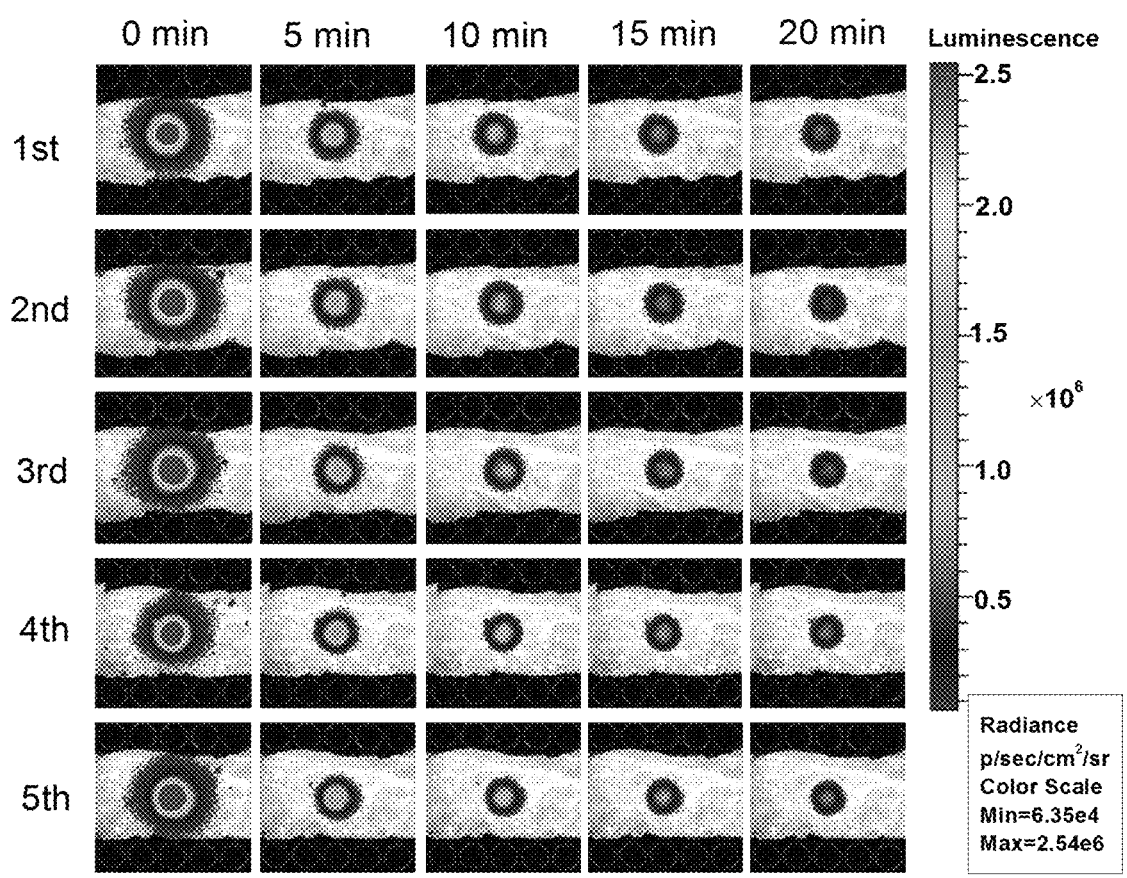
FIG. 5. Recharged in vitro PL imaging of mZGC covered by an 8-mm pork layer.
Figure 10:
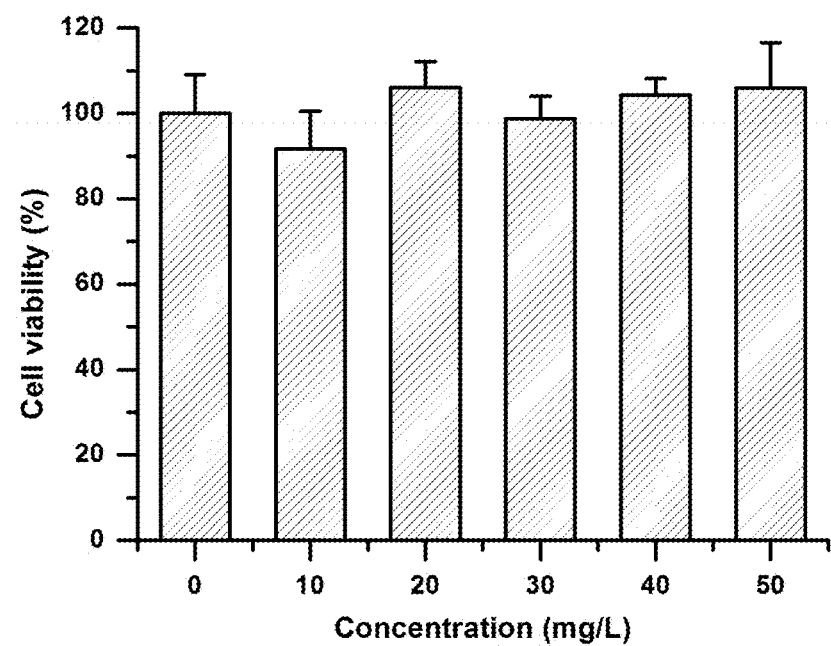
FIG. 10. Cell toxicity of mZGC. The cytotoxicity was tested using 3-(4,5-dimethyl-2-thiazolyl)-2,5diphenyl-2H-tetrazolium bromide (MTT, sigma, USA) assay using human umbilical vein endothelial cells (HUVE cells, ATCC, CRL-1730).
Figure 11:
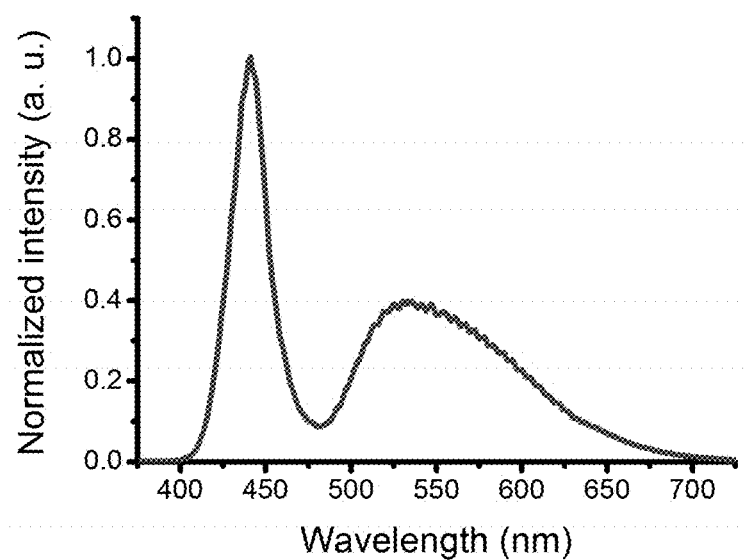
FIG. 11. Spectrum of the LED torch used in experiments. Wavelengths longer than 600 nm have better biological tissue penetration ability than shorter ones, and result in the charging of mZGC in vivo.

With the demonstration that the PL of mZGC can be charged by red light under an 8 mm pork layer, for the first time its applications are studies in deep-tissue imaging using a white light-emitting diode (LED) as the excitation light source (spectrum shown in FIG. 11). The rechargeable PL imaging of the mZGC sample was performed five times under a pork layer of 8 mm without any obvious signal weakening, which implies its potential for use in in vivo imaging applications (FIG. 5). For in vivo applications, good biocompatibility is anticipated since the NIR PL phosphor, ZGC, is mainly incorporated within the mesopores of the MSNs, which are well-known to be biocompatible. No apparent cellular toxicity were observed for mZGC under an exposure concentration as high as 50 mg/L (FIG. 10).

Figure 6:
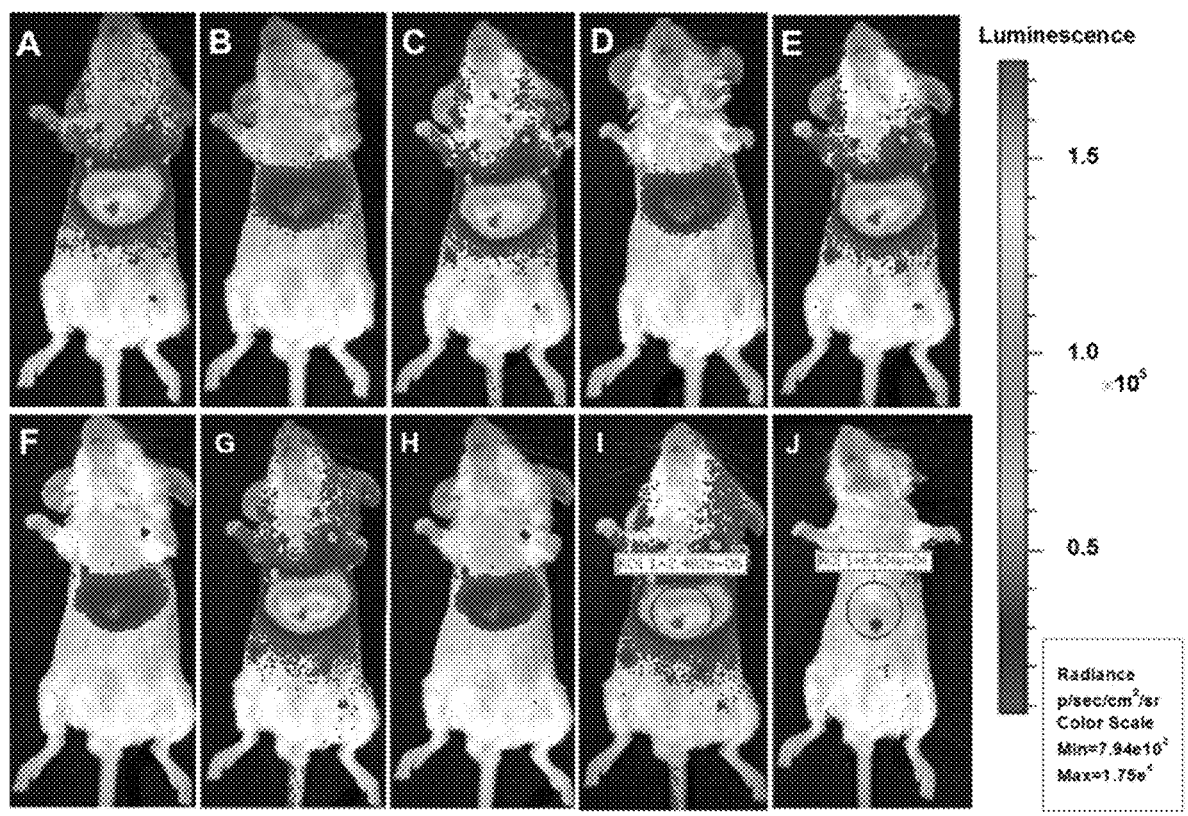
FIG. 6. In vivo recharging of mZGC for PL imaging using a white LED. (A) First charging, (B) 10 min after first charging, (C, E, G, I) second to fifth recharging at time intervals of 10 min, (D, F, H) 10 min after second, third, and forth recharging, (J) background control imaging of a mouse without injection of mZGC.
Figure 7:
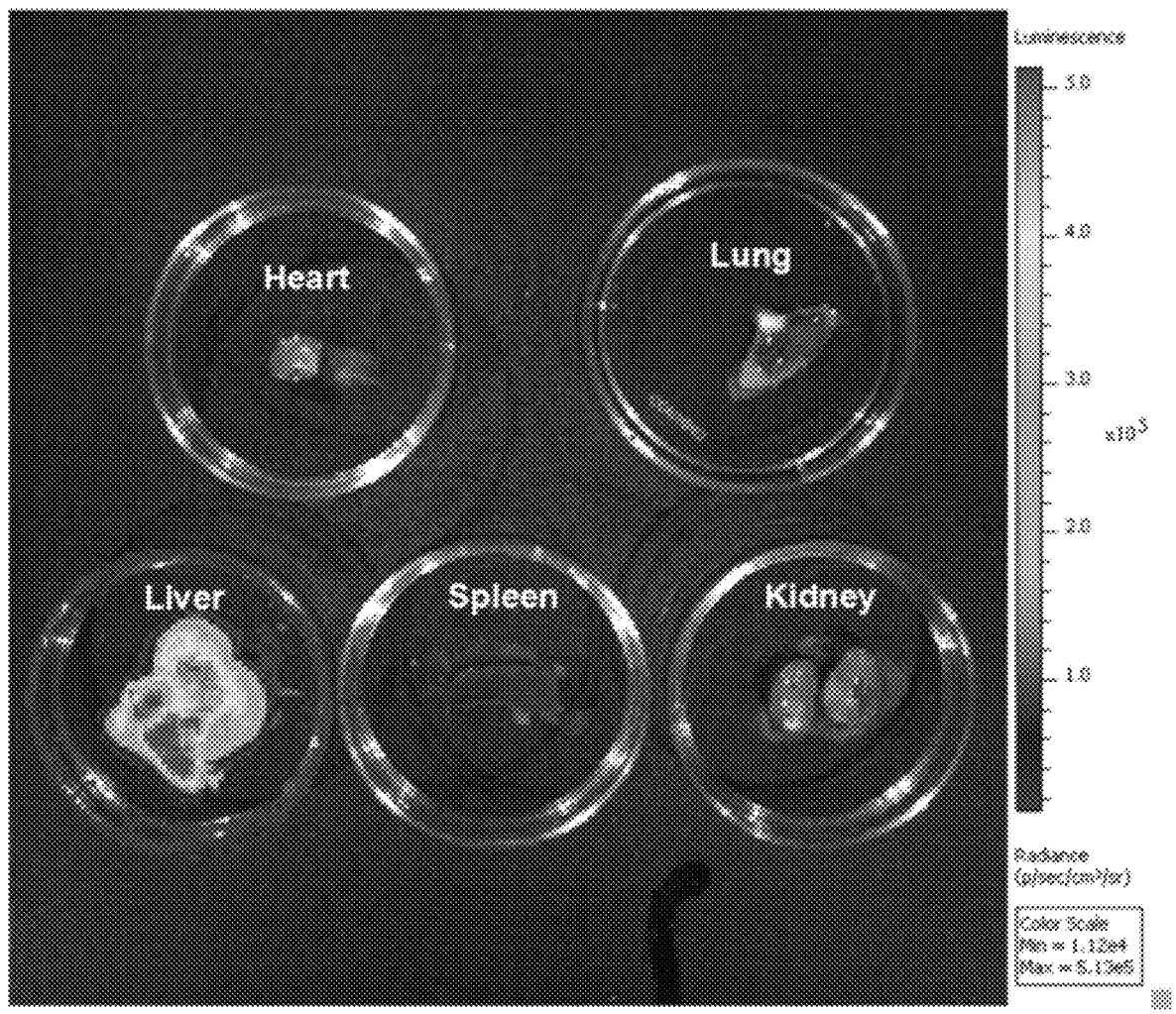
FIG. 7. Biodistribution of mZGC, 2 h after tail-vein injection.

To study the in vivo chargeability of mZGC, the mZGC saline solution (200 μL, 5 mg/mL) was injected into a live mouse through the tail vein. After exposure to white LED light, a satisfactory PL imaging picture was obtained, as shown in FIG. 6. Moreover, after re-performing the in situ excitation, the PL of ZGC was recharged again. No apparent decrease in PL signal was observed after five imaging/recharging cycles (FIG. 6). A high signal-to-noise ratio of ~40:1 was obtained by comparing the PL signal from liver area of mouse with and without injecting mZGC. The biodistribution of the mZGC was studied after euthanasia of the mouse (2 h after injection). Most of the PL signals emanate from the liver and spleen, which is consistent with the in vivo imaging results (FIG. 7). Given the in vivo chargeable PL attributes, the detection of the PL functionalized mesoporous carriers in vivo is not limited by the decay of the PL intensity. Thus, the as-synthesized mZGC has great potential to become a new class of mesoporous nanocomposites with NIR PL properties.

Thus, disclosed herein is an in vivo rechargeable NIR-emitting mesoporous $SiO_2/ZnGa_2O_4:Cr^{3+}$ PL nanocomposites. By using the mesopores of MSNs as a reaction template, the synthesis temperature of the persistent phosphor, $ZnGa_2O_4:Cr^{3+}$ was decreased from higher than 750° C. in a solid-state reaction to only 600° C. At this lower temperature, both the unique mesoporous attributes, and the uniform size and morphology of the MSNs were retained in the nanocomposites. For the first time, it was confirmed that mZGC could be repeatedly charged in situ under a deep-tissue layer of 8 mm. The deep-tissue chargeable PL properties of mZGC also ensured its repeatable recharged PL imaging in a live mouse model. It is worth noting that this observation is the first direct evidence that persistent luminescence can be recharged in vivo for multiple times. This concept of utilizing mesoporous silica as nanoreactor to fabricate ZGC PL nanoparticles with uniform morphology and preserved porous nanostructure will be significant in directing the synthesis of mesoporous PL systems with diverse PL phosphors and paves a new way to the wide application of deep tissue rechargable ZGC in photonics and biophotonics.

Experimental

Materials

Tetraethoxysilane (TEOS), ethanol, diethanolamine (DEA), ammonium hydrate, cetyltrimethylammonium bromide (CTAB), $Ga_2O_3$, $Zn(NO_3)_2 \cdot 6H_2O$, $Cr(NO_3)_3 \cdot 9H_2O$, and concentrated nitric acid were all of analytical standards, purchased from Sigma-Aldrich and were used as-received. Ga(NO$_3$)$_3$ solution was prepared by dissolving Ga$_2$O$_3$ in 1:1 concentrated nitric acid followed by air drying at 105° C. to remove excess nitric acid, and then redissolving in deionized water.

Synthesis of MSNs

The MSN synthesis was modified from that in a previous report. (Zhan-Jun, et al. 2012 *J Mater Chem* 22, 24713.) Briefly, 7 mL of ethanol, 0.2 g of CTAB, and 50 µL of diethanolamine were dissolved in 25 mL of water under stirring at 60° C. for 30 min to prepare a transparent solution. Then, 2 mL of tetraethoxysilane were added rapidly. The reaction was finished after stirring for another 2 h. Mesoporous silica nanospheres (about 100-nm diameter) were collected by centrifugation and calcination at 550° C. for 2 h to remove CTAB and possible organic residues.

Synthesis of mZGC Nanocomposites

A precursor solution was prepared by dissolving the corresponding nitrates in water/ethanol (1/1, v/v). The final concentration of $Zn^{2+}$, $Ga^{3+}$, and $Cr^{3+}$ was controlled to be 0.5 mol/L, 0.9985 mol/L, and 0.0015 mol/L, according to a stoichiometric ratio of Zn/Ga/Cr (1/1.997/0.003, molar ratio), respectively. 200 µL of the precursor solution were mixed with 200 mg mesoporous silica and the mixture was dried in a vacuum oven at 50° C. for 12 h. The samples were then put into a muffle furnace and the temperature was slowly increased by 5° C./min.

In Vitro and In Vivo PL Imaging of mZGC

In vitro imaging was performed by putting the powder (100 mg) sample into a black 96-well plate covered with an 8-mm layer of pork tissue. The PL signal from the covered mZGC was recorded after illumination using an LED (5000 lumen) for 15 s. The in vivo imaging was conducted by injection of the mZGC dispersion in phosphate-buffered saline (PBS; 5 mg/mL) through the tail vein. The sample was stored in a dark box for 1 day before injection to ensure no pre-activation occurred.

Characterization

X-ray powder diffraction (XRD) measurements were performed on a diffractometer equipped with Cu Kα radiation (λ=1.5418 Å) (Panalytical X'pert PRO, The Netherlands). The morphology of the samples was inspected using field-emission scanning electron microscopy (FESEM, HITACHI S-4800, Japan) and transmission electron microscopy (TEM, HITACHI H-7650, Japan) at accelerating voltages of 5 and 100 kv, respectively. High-resolution TEM (HRTEM) images were recorded using a JEM-1200EX II transmission electron microscope. N$_2$ adsorption/desorption isotherms were obtained on a full-automatic physical and chemical adsorption apparatus (micromeritics, ASAP2020C, USA). Pore size distribution was calculated from the adsorption branch of N$_2$ adsorption/desorption isotherm and the Brunauer-Emmett-Teller (BET) method. The BET specific surface areas were calculated using the data between 0.05 and 0.35 just before the capillary condensation. The total pore volumes were obtained by the t-plot method. Total organic carbon analyzer was used to determine the exact loading level of ibuprofen on mZGC using a CNS elemental analyzer (Elementar Portfolio, Vario MAX, Germany). The spectra and lifetimes of the samples were tested using powdered samples. The photoluminescence spectra and time-decay curves were measured using a fluorospectrophotometer (FluoroMax-3, HORIBA, USA). The absorbance was detected on a UV-vis spectrometer (Thermo, Evolution300, USA). The PL imaging of mZGC was conducted in a Xenogen IVIS imaging system.

II. Facile Solution-Phase Chemical Synthesis of NIR Persistent Luminescence Nanocrystals Hydrothermal synthesis refers to the synthesis by chemical reactions of substances in a sealed heated solution above ambient temperature and pressure. This technique is considered to be one of the widely used technologies to produce nanocrystals (Shi, et al. 2013 *Chem Soc Rev* 42, 5714.)

Existing fabrication of NIR ZGC PLNPs must undergo solid-state-annealing method at extreme high temperatures and complicated physical methods have to be used to convert as-synthesized large bulk crystals into nanosized particles. As the result, these particles are usually heterogeneous, relative larger, and form agglomerates fast in solution. In addition, a key requirement for bioimaging applications is that the nanocrystals be biocompatible, which means that they need to be comparable in size to the biomolecules they are labeling, so as not to interfere with cellular systems. To date, however, there has been no report of direct aqueous-phase chemical synthesis of NIR PL materials, not to mention sub-10 nm nanoparticles.

Figure 12:
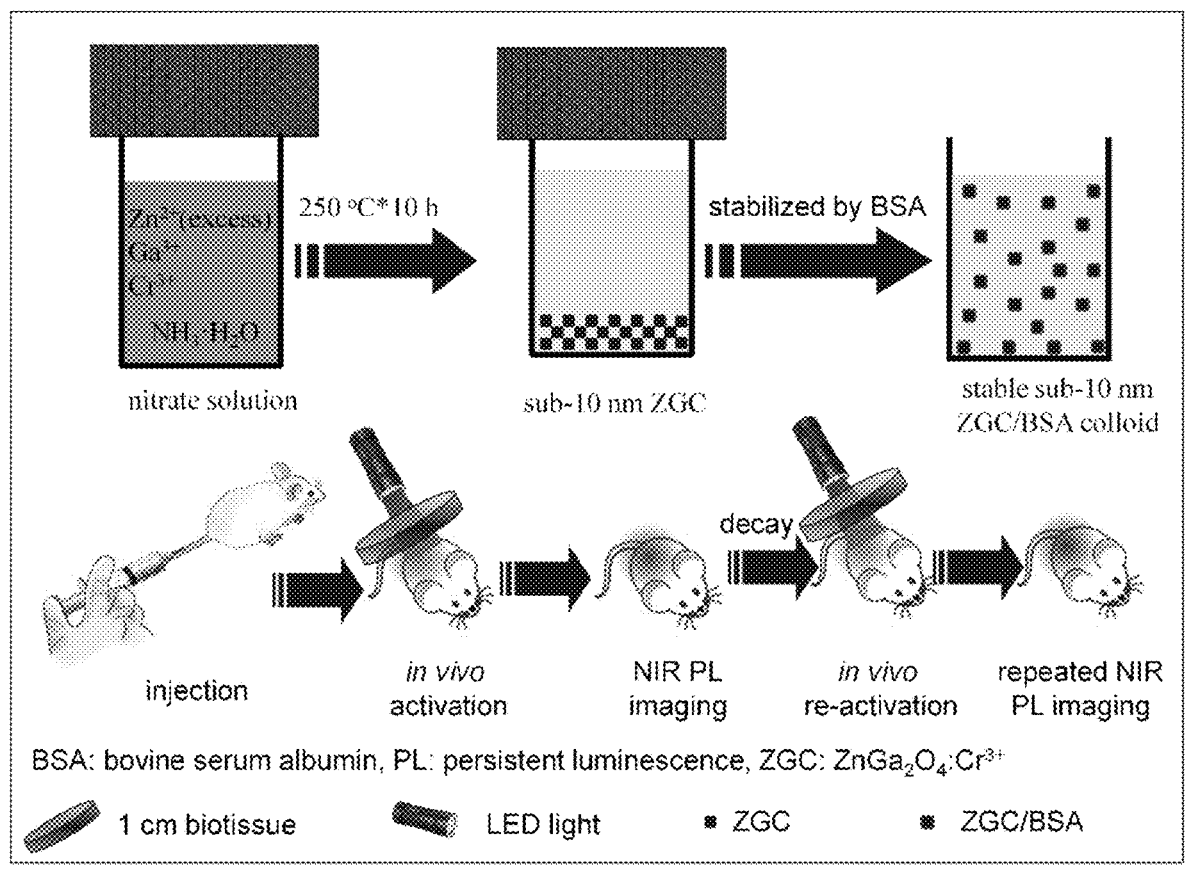
FIG. 12. Schematic illustration of the synthesis and imaging applications of ZGC PLNPs.

As disclosed herein, water-soluble ZnGa$_2$O$_4$Cr$_{0.004}$ PLNPs, with sub-10-nm size and intense PL properties were directly synthesized in aqueous solution by hydrothermal method. An initially attempt was to prepare PLNPs by dissolving Zn(NO$_3$)$_2$, Ga(NO$_3$)$_3$, and Cr(NO$_3$)$_3$ precursor solutions in a sealed Teflon-lined autoclave and underwent a hydrothermal processing at 250° C. for 10 h (FIG. 12). ZGC PLNPs were generated with a narrow size distribution and an average size of 8±4 nm (denoted as ZGC-1; FIG. 13A). The ultra-small size was further confirmed by analysis of the full width at half maximum values of the XRD diffraction peaks and by the Schërrer equation, with an average calculated particle size of 8.7±2.4 nm. As shown in FIG. 13B, as-synthesized ZGC-1 has a clear lattice fingerprint of a (311) plane of cubic ZnGa$_2$O$_4$. The selected area's electron diffraction pattern (SAED) result, shown in FIG. 13C, indicates that the ZGC nanoparticles have a clear crystal structure and that all of the diffraction circles can be attributed to cubic ZnGa2O4. The formation of pure ZnGa2O4 was also confirmed by analysis of its XRD pattern to that of standard data (JCPDS card, no. 01-082-0466; FIG. 13D).

A stable dispersed colloidal solution is usually a premise for the surface modification of nanoparticles. Unfortunately, the re-dispersion of ZGC synthesized by conventional solid state annealing reaction (ZGC-2) is quite difficult due to the severe agglomeration caused by high temperatures. In contrast, the as-synthesized ZGC-1 can be re-dispersed (or "dissolved") easily in water forming a transparent colloidal solution after a simple acid treatment. Dynamic light scattering analysis was used to analyze the storing stability of ZGC-1. No significant change was observed in the hydrodynamic size distribution of ZGC-1 colloid even after storing for one month (FIG. 14A). In contrast to the as-synthesized ZGC-1, apparent precipitation were observed 30 minutes after milling and ultrasonic treatment of the ZGC dispersion, which was synthesized according to high temperature annealing method (ZGC-2) (FIGS. 14B and 14C).

Figure 15:
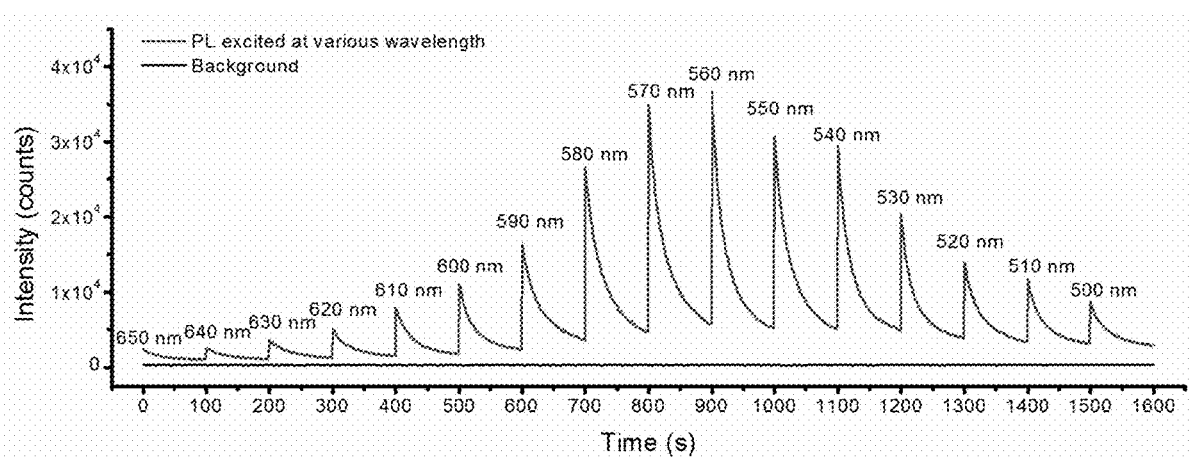
FIG. 15. Decay curves of ZGC-1 excited by various wavelength.
Figure 16:
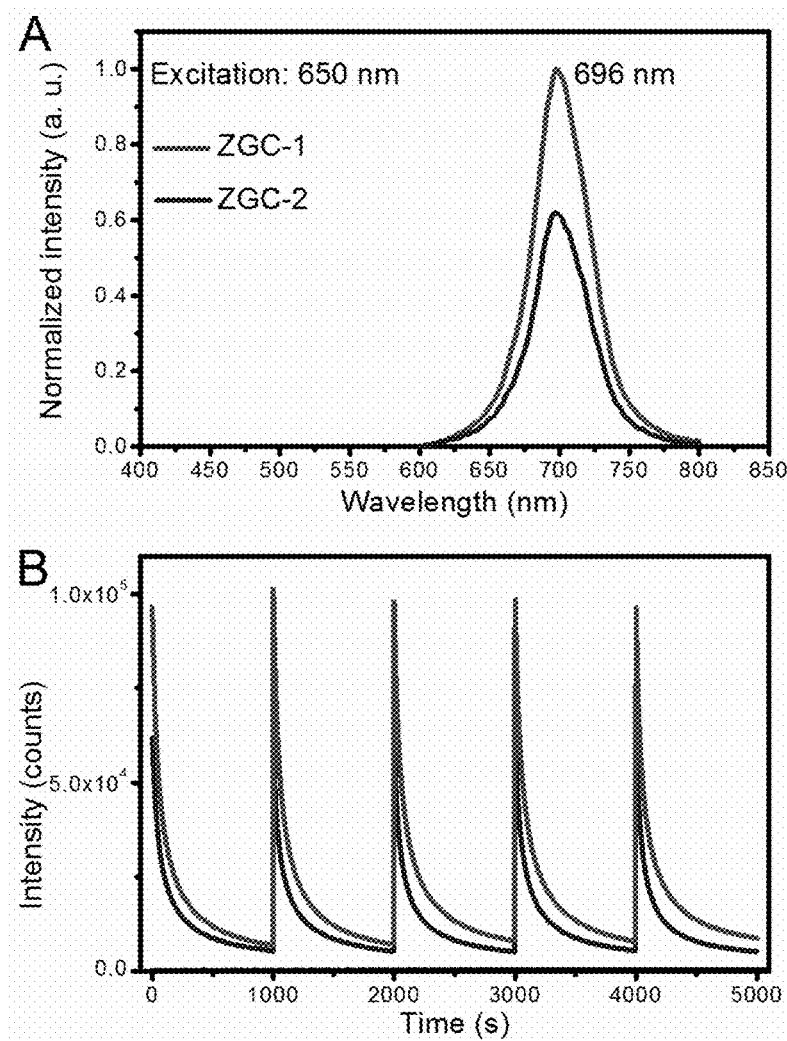
FIG. 16. Superior PL properties of ZGC-1. (A) PL spectra and (B) decay curves of ZGC-1 and ZGC-2 excited at 650 nm for 200 s using a xenon lamp as the light source. PL spectra and decay curves were recorded 30 s after the stop of the excitation. Sample mass=100 mg.

Further systematically studied were the PL properties of ZGC-1 under diverse excitation wavelengths ranging 500-650 nm using the xenon lamp in a fluorimeter as the light source without any corrections made (FIG. 15). The results indicated that the PL decay curves of the ZGC-1 can be excited by wavelengths as far as 650 nm. Importantly, during five repeated excitation and decay cycles at 650 nm, it was found that the PL intensity of ZGC-1 was nearly double relative to ZGC-2 30 s after the stop of the excitation (FIG. 16).

A comparison imaging experiment was performed both in vitro and in vivo using a commercial white LED (5000 lumen, CREE-T6) as light source. By applying the ROI tools of the imaging device, the charging ability of ZGC-1 vs ZGC-2 was compared. The in vitro imaging results indicate an increase of PL intensity of ZGC-1 by a factor of 2.7, as shown in FIG. 17A. While the in vivo results indicate a factor of 2.0 for ZGC-1, as shown in FIG. 17B. Simulated deep-tissue imaging was further performed with live mouse models covered by a pork slab~1 cm thick. The PL of ZGC-2 could hardly be observed under our simulated deep-tissue environment, whereas ZGC-1 still provided clear, quality images (FIGS. 18A and 18B). The PL signal is eliminated completely 30 min after excitation without influencing the next imaging cycle. Once again, it can be reactivated at a desired time to provide PL images (FIGS. 18C-18H).

Figure 19:
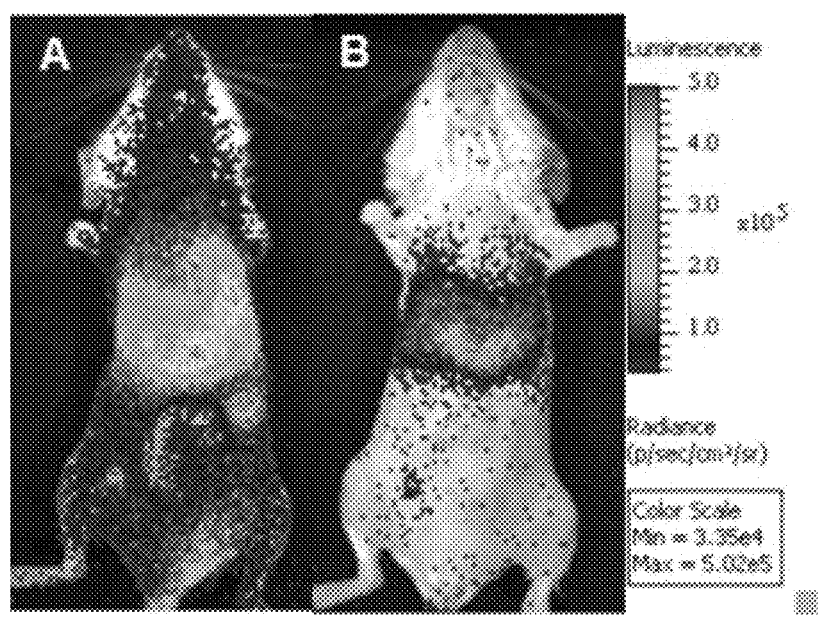
FIG. 19. Imaging applications of ZGC PLNPs after ex vivo (A) and in vivo (B) being excited using a white LED light source (5000 lumen).
Figure 20:
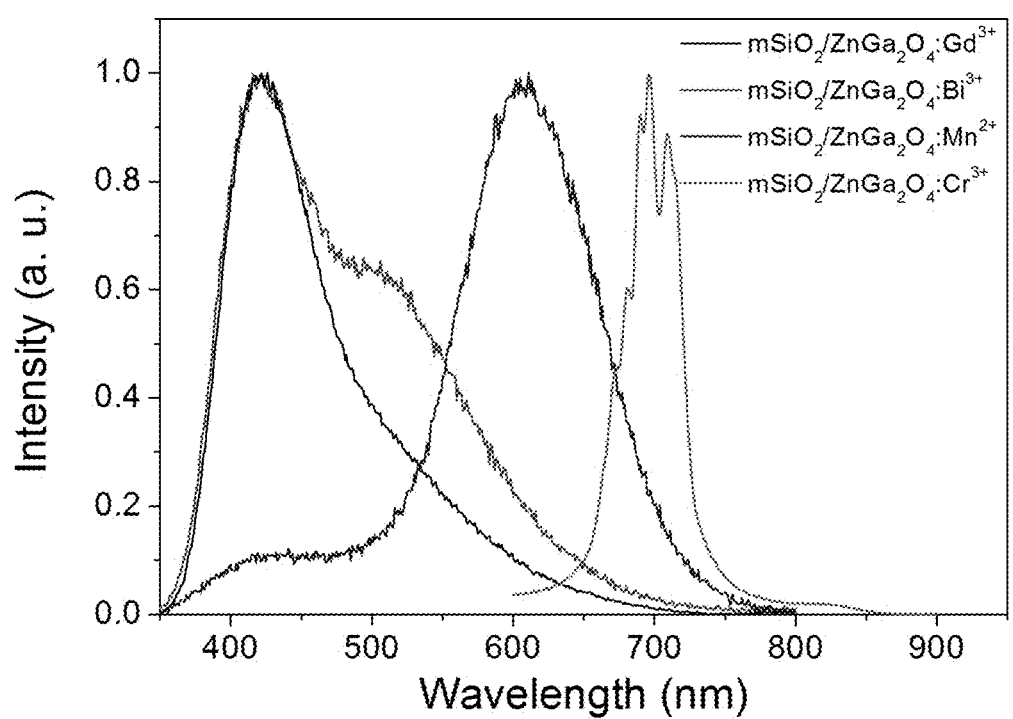
FIG. 20. Luminescence spectra of PLNPs, $mSiO_2$/$ZnGa_2O_4$ doped with diverse dopant ions.

Based on our observations, ZGC-1 is more suited to deep-tissue imaging applications. The in vivo imaging performance of ZGC-H was also performed using a live mouse model (FIG. 19). The PL of ZGC-1 could be applied to track its bio-distribution in live mouse. After the ex vivo charged PL was exhausted, the PL emission could be recharged in vivo by illumination the mouse with a white LED. Although the intensity is relatively weak than that excited ex vivo, the total traceable time was not limited by the decay attribute of persistent phosphor. More importantly, it was found that the ZGC-1 PLNPs can be in vivo activated through bony structure after being injected inside the spinal tube. The PL imaging result in the live mouse model is consistent with the one performed after open the spinal bone, indicating potential applications in the central neural system or any imaging application through the bone.

Experimental

Materials $Ga_2O_3$, $Zn(NO_3)_2 \cdot 6H_2O$, $Cr(NO_3)_3 \cdot 9H_2O$, ammonium hydroxide, hydrochloride acid, and concentrated nitric acid were all analytical reagents and used as received. $Ga(NO_3)_3$ solution was prepared by dissolving $Ga_2O_3$ in 1:1 concentrated nitric acid followed by air drying at 105° C. to remove the excess amount of nitric acid and re-dissolved in deionized water. 1 mol/L $Zn(NO_3)_2$, 2 mol/L $Ga(NO_3)_3$, 4 mmol/L $Cr(NO_3)_3$ were stored as precursor solution. A little nitric acid was used to prevent hydrolysis of $Ga(NO_3)_3$. Polyethyleneimine (PEI) and bovine serum albumin (BSA) were purchased from Sigma-Aldrich and used directly without further purification.

Synthesis of ZGC-1 by Hydrothermal Process

A certain amount of $Ga(NO_3)_3$ (2 M), $Zn(NO_3)_2$ (1 M), $Cr(NO_3)_3$ (4 mM) precursor solution were mixed with pre-determined molar ratio to form a precursor solution. Ammonium hydroxide (28%, wt) was added quickly under vigorous stirring to reach a pH of 9. The metal hydroxide precursor was sealed into a Teflon-lined autoclave and then performed hydrothermal process at 220° C. for 10 hours. ZGC nanocrystals can be obtained within a wide total concentration molar ratio of precursor, which influenced the product sizes and distributions. In a typical procedure, 2 mmol of $Zn(NO_3)_2$, 2 mmol of $Ga(NO_3)_3$, 0.004 mmol $Cr(NO_3)_3$ were mixed together under vigorous stirring. The total volume was adjusted to 15 mL by adding deionized water. Concentrated ammonium hydroxide (28%) solution (about 1 mL) was added rapidly to adjust the pH to be 9-9.5. White precipitate was formed immediately. After further stirring for half an hour, the mixture were transmitted into a Teflon-lined autoclave (25 mL) and sealed. The autoclave was put in an oven at 220° C. for 10 hour and then cooled to room temperature naturally. The white precipitate could be obtained easily by centrifugation. The product could be dispersed in 0.01 M HCl forming transparent solution. Possible ZnO impurity could be removed by acid washing. ZGC nanocrystals could be obtained by centrifugation after diluted with excess isopropanol. Finally, ZGC nanocrystals were redispersed in deionized (DI) water for further characterization and imaging application. The storing concentration of ZGC is approximately 4 mg/mL and used for further modification.

For the dispersion in cell culture medium, 200 μL ZGC-1 storing solution was first diluted with 1 mL water and then added into 5 mL of cell culture medium drop by drop under stirring. A clear solution can be obtained after 10 min ultrasonic dispersion.

PEI could be adsorbed to the crystal surface of ZGC-1 due to the electrostatic interaction with the negatively charged ZGC-1 nanocrystals, forming PEI modified ZGC (ZGC/PEI). Briefly, 1 mL of ZGC-1 storing solution was added into 10 mL 1 mM of HCl solution, and stirring for 30 min. 1 mL of PEI solution (20%, wt) was then added rapidly under vigorous stirring. ZGC-PEI could be collected by centrifugation after diluted with excess isopropanol. ZGC-PEI was redispersed in DI water under ultrasonic dispersion.

ZGC-1 was also modified with BSA. 1 mL of ZGC-1 solution (4 mg/mL) was added into 10 mL of BSA solution (1% by weight) drop by drop under stirring followed by further stirring for another 30 min. BSA modified ZGC-1 (ZGC-BSA) was collected by centrifugation and redispersed in 10 mL of DI water by ultrasonic dispersion.

Synthesis of ZGC-2 by Hydrothermal Assisted Solid State Annealing Method

GC-2 was synthesized for comparison according to reported hydrothermal assisted annealing method. 1 mmol of $Zn(NO_3)_2$, 2 mmol of $Ga(NO_3)_3$, 0.004 mmol $Cr(NO_3)_3$ were mixed together under vigorous stirring. The total volume was adjusted to 10 mL by adding deionized water. Concentrated ammonium hydroxide (28%) solution (about 1 mL) was added rapidly to adjust the pH to 7.5. The mixture was sealed into a Teflon-lined autoclave at 120° C. for 24 hour. The resulting precipitate has no PL properties and was sintered at 750° C. for 5 hours. A small amount of 5 mM NaOH solution was added to the powder product to form a slurry followed by wet grinding for 1 hour with a mortar and pestle. The product was washed by ethanol (90%) and then dried at 60° C.

Synthesis of ZGC-3 by Using Hydrothermal Post-Treatment he as-synthesized ZGC-2 was mixed with ammonium aqueous solution (pH 9~9.5) and sealed in an autoclave, which underwent a hydrothermal procedure at 220° C. for 10 hours. The as-synthesized ZGC-3 was centrifuged and dried at 80° C.

Imaging

A white LED (5000 lumen, CREE-T6) was used for all the imaging experiments as the light source. For the in vitro experiment, 50 mg of ZGC sample was put in one well of a black 96-well-plate. The plate was exposed to the LED for 30 s and then put into the IVIS imaging system to detect the PL signal. The in vivo imaging was performed after subcutaneous injection of the sample dispersion (50 μL, 2 mg/mL) and 30 s of in situ LED excitation. The in vivo deep tissue recharged PL of ZGC was performed by covering the subcutaneous injection site with a 1-cm pork slab. The imaging was performed immediately after 30 s of in situ LED excitation.

Figure 13:
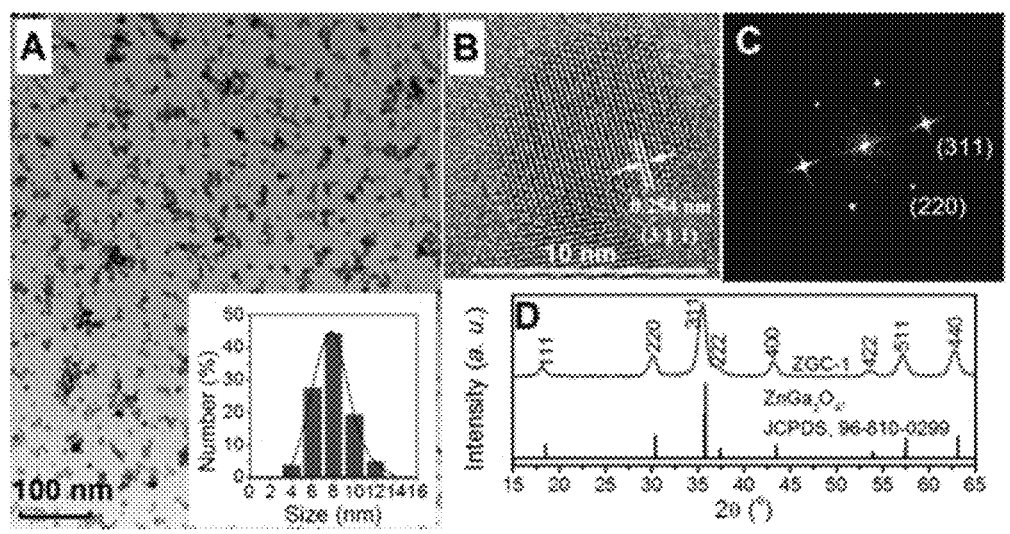
FIG. 13. (A) TEM and size distribution, (B) HRTEM, of a single crystal, (C) selected area electron diffraction pattern, and (D) X-ray diffraction analysis of ZGC-1.
Figure 14:
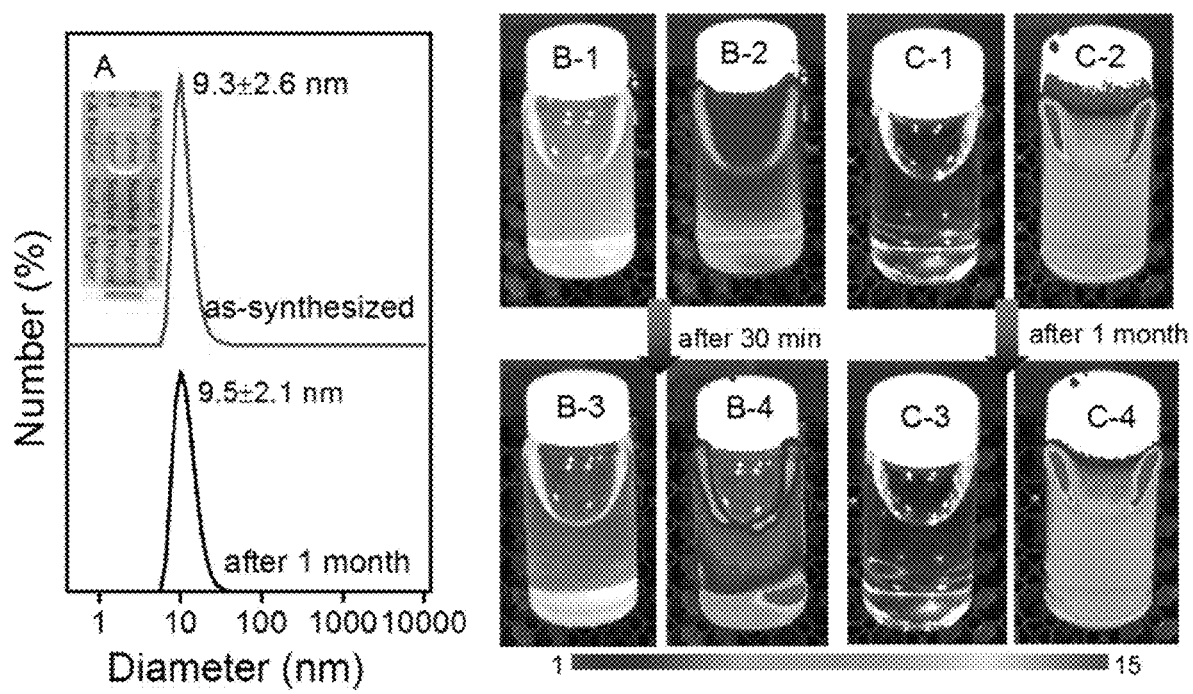
FIG. 14. The disperse stability of ZGC-1 and ZGC-2 in water (pH=6.5). (A) Dynamic light scattering patterns of ZGC-1 in water before and after storage of 1 month, (B1, B3) bright field and (B2, B4) corresponding luminescence pictures of ZGC-2 in water, (C1, C3) bright field and (C2, C4) corresponding luminescence pictures of ZGC-1 in water. Persistent luminescence intensity is expressed in false color units (1 unit=2.107 photons·s−1·cm−2·sr) for all images.
Figure 17:
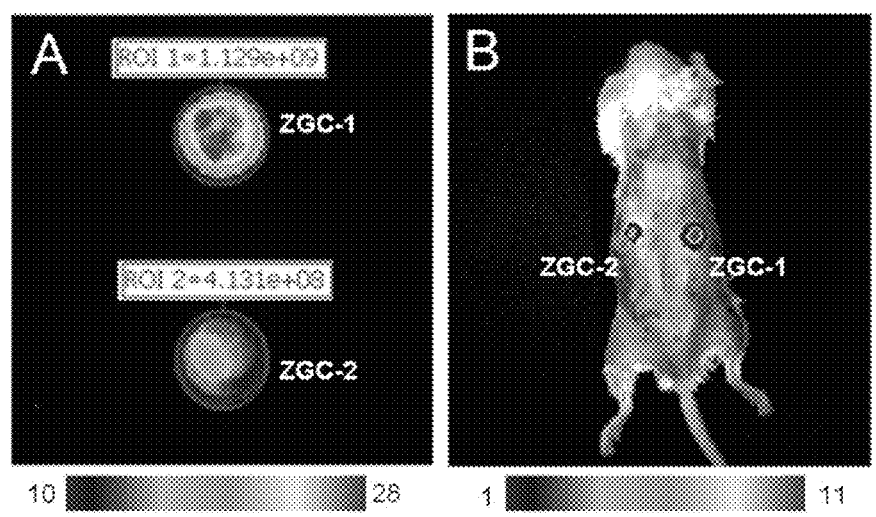
FIG. 17. Analysis of the imaging ability of ZGC-1 and ZGC-2. (A) 50 mg in a black 96-well-plate; (B) in vivo activated imaging after subcutaneous injection (50 μL, 2 mg/mL). Persistent luminescence intensity is expressed in false color units (1 unit=1·$10^6$ photons $s^{-1}·cm^{-2}·sr$) for all images.
Figure 18:
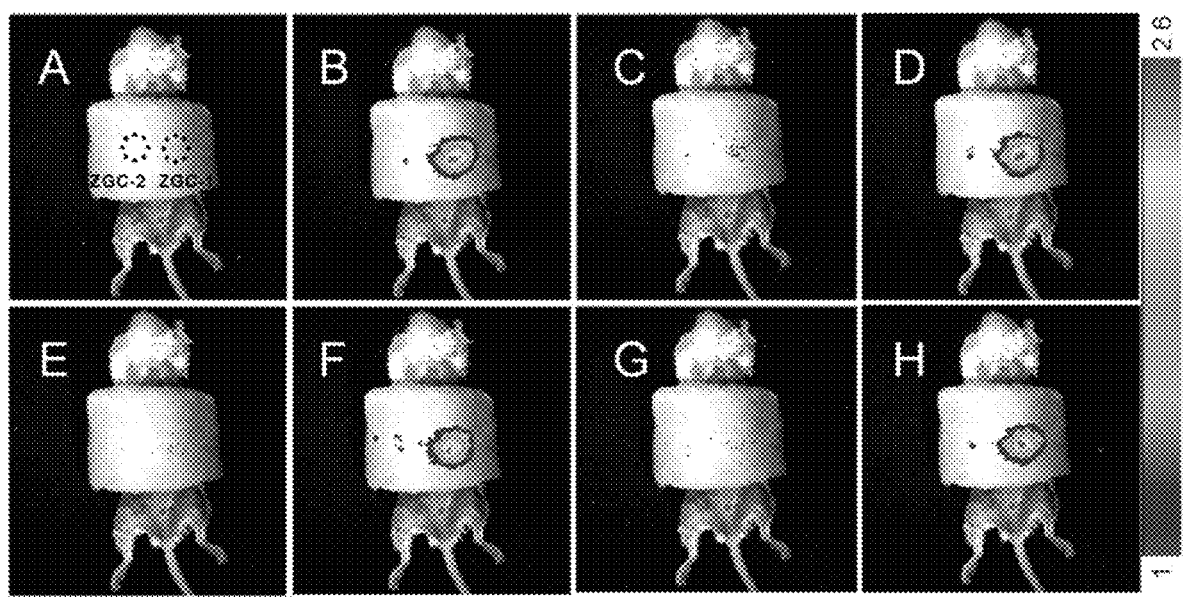
FIG. 18. Comparative deep tissue imaging of ZGC-1 and ZGC-2. (A and B) deep tissue in vivo imaging before and after in situ excitation; (C-H) repeated imaging before and after 2nd, 3rd, and 4th in situ excitations, time interval=30 min. Excitation with a white LED (5000 lumen) light source for 30 s. Persistent luminescence intensity is expressed in false color units (1 unit=4350 photons $s^{-1}·cm^{-2}·sr$) for all images.

Thus, a novel aqueous phase-based synthetic methodology has now been demonstrated for the preparation of uniformed NIR PL ZGC nanoparticles that can be homogenously dispersed in an aqueous solution or suspension. The synthesis temperature was significantly decreased from up 1000° C. to 250° C., which greatly simplifies the reaction equipment. The as-synthesized ZGC nanocrystals can be made as small as a size of 8±4 nm with narrow size distribution, which is important for its potential biomedical applications (FIG. 13). The ZGC-1 product can be easily dispersed into water after a simple acid washing post-treatment, which will facilitate its surface modification of diverse functional group including biomolecules (e.g., antibody)(FIG. 14). The ZGC-1 product can be activated in deep tissue covered by 1 cm pork layer, which will facilitate its applications in animal models (FIG. 18). The ZGC-1 has shown significantly superior PL intensity than that synthesized using traditional annealing method (FIG. 16-18).

The luminescence color of the PLNPs can be further tuned by altering the dopant ions, such as, $Gd^{3+}$ (blue), $Bi^{3+}$ (white), $Mn^{2+}$ (orange) and $Cr^{3+}$ (near-infrared). Due to the uniform morphologies and ultra-small sizes, persistent luminescence nanoparticles disclosed herein can be easily dispersed into various solvents, such as water, ethanol, ethyl acetate.

LNPs disclosed herein may be used in biomedical application. The NIR persistent luminescence mZGC may be developed as an in vivo traceable drug delivery system. PLNPs can also be used in tumor imaging. As no excitation will be needed during the imaging procedure, high quality imaging result can be obtained by removal of the bio-autofluorescence caused by excitation. mZGC disclosed herein can not only provide tumor imaging ability but also can carry load of functional molecules such as gene, protein, theronostic reagents.

LNPs may be applied in versatile applications in addition to their vast utilities in the healthcare and medical research. For example, they can be dispersed easily into solutions such as nitrocellulose ethyl acetate solution, which is the main content of most commercial nail polish. Also, the PLNPs can be dispersed in polyvinyl acetate/ethanol solution, which is a common solvent used in hair spray. The addition of persistent luminescence nanoparticles in nail polish or hair spray will form colorful afterglow emissions. At night or wherein the light is dark, the afterglow emission can form cool, beautiful nails or hair. Similar applications may also be found in shoe polish, hair spray, art pigment, etc.

Visible persistent luminescence materials have found application as afterglow fingermark powders used with the visualization of latent fingermarks deposited on multicolored substrate surfaces that can present a contrast problem if developed with regular fingermark powders. Persistent phosphors can provide a strong afterglow effect which aid in the establishment of better fingermark detection. Regard the NIR persistent phosphor, such as our synthesized mZGC, the mZGC disclosed herein can not only image the latent fingermark but also be utilized in information encryption. If mZGC is printed on papers, the NIR persistent luminescence cannot be seen by naked eyes. The NIR luminescence can only be visualized by using special NIR imaging instrument. Thus, NIR persistent luminescence has great potential in the field of information encryption and counterfeit labels.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A method for preparing persistent luminescence nanoparticles, comprising conducting a hydrothermal chemical reaction in an aqueous phase under conditions sufficient to form uniform and homogeneous persistent luminescence nanoparticles, wherein conducting a hydrothermal chemical reaction comprises:
   providing an aqueous solution comprising $Zn(NO_3)_2$, $Ga(NO_3)_3$, and $Cr(NO_3)_3$ in a sealed autoclave; and
   conducting the hydrothermal chemical reaction is conducted in aqueous phase at a temperature from about 150° C. to about 300° C. thereby forming $ZnGa_2O_4$:Cr persistent luminescent nanoparticles with substantially uniform particle size of less than about 20 nm.

2. The method of claim 1, wherein the hydrothermal chemical reaction is conducted in aqueous phase at a temperature from about 150° C. to about 250° C. for 10 hours.

3. The method of claim 2, wherein the formed persistent luminescent nanoparticles are substantially uniform with a median particle size of less than about 10 nm.

4. The method of claim 3, wherein the persistent luminescence nanoparticles are NIR-emitting in the range of 650 nm and 900 nm.

5. The method of claim 4, wherein the mesoporous persistent luminescence nanoparticles are pure crystalline doped zinc gallates $ZnGa_2O_4$:Cr.

6. The method of claim 4, wherein persistent luminescence is detectable at least 5 hours after excitation.

7. The method of claim 6, wherein persistent luminescence is detectable at least 10 hours after excitation.

\* \* \* \* \*